United States Patent
Högdahl

(10) Patent No.: US 10,286,157 B2
(45) Date of Patent: May 14, 2019

(54) AUTO-INJECTOR WITH PIVOTING TRIGGER

(71) Applicant: Carebay Europe Ltd, Sliema (MT)

(72) Inventor: Stefan Högdahl, Stockholm (SE)

(73) Assignee: SHL MEDICAL AG, Zug (CH)

( * ) Notice: Subject to any disclaimer, the term of this patent is extended or adjusted under 35 U.S.C. 154(b) by 313 days.

(21) Appl. No.: 15/031,730

(22) PCT Filed: Oct. 22, 2014

(86) PCT No.: PCT/EP2014/072670
§ 371 (c)(1),
(2) Date: Apr. 23, 2016

(87) PCT Pub. No.: WO2015/059201
PCT Pub. Date: Apr. 30, 2015

(65) Prior Publication Data
US 2017/0224928 A1    Aug. 10, 2017

(30) Foreign Application Priority Data
Oct. 25, 2013    (SE) .................................... 1351274

(51) Int. Cl.
| | | |
|---|---|---|
| *A61M 5/315* | (2006.01) | |
| *A61M 5/20* | (2006.01) | |
| *A61M 5/46* | (2006.01) | |
| *A61M 5/31* | (2006.01) | |

(Continued)

(52) U.S. Cl.
CPC ...... *A61M 5/31571* (2013.01); *A61M 5/2033* (2013.01); *A61M 5/3137* (2013.01); *A61M 5/31501* (2013.01); *A61M 5/31576* (2013.01); *A61M 5/3202* (2013.01); *A61M 5/3204* (2013.01); *A61M 5/3245* (2013.01); *A61M 5/46* (2013.01); *A61M 2005/202* (2013.01);

(Continued)

(58) Field of Classification Search
CPC ............ A61M 5/31571; A61M 5/2033; A61M 5/3137; A61M 5/31501; A61M 5/31576; A61M 2005/202; A61M 2005/206; A61M 2005/208; A61M 2005/2407
See application file for complete search history.

(56) References Cited

U.S. PATENT DOCUMENTS

| | | | |
|---|---|---|---|
| 4,194,505 A | 3/1980 | Schmitz | |
| 5,599,309 A | 2/1997 | Marshall et al. | |
| 6,203,530 B1 | 3/2001 | Stewart, Sr. | |

FOREIGN PATENT DOCUMENTS

| | | |
|---|---|---|
| GB | 2452286 A | 3/2009 |
| GB | 2487235 A | 7/2012 |
| GB | 2488579 A | 9/2012 |

OTHER PUBLICATIONS

EPO, Int'l Search Report in PCT/EP2014/072670, dated Feb. 19, 2015.

*Primary Examiner* — Kevin C Sirmons
*Assistant Examiner* — Leah J Swanson
(74) *Attorney, Agent, or Firm* — McDonnell Boehnen Hulbert & Berghoff LLP

(57) ABSTRACT

A resettable and reusable auto-injector with a trigger having a pivot axis dividing an elongate body into distal and proximal portions. The proximal portion has a finger surface on an upper section and a bearing surface projecting downwardly configured to engage a button blocker to function as a safety feature to prevent premature firing of the auto-injector before a needle hider is pressed against an injection site.

19 Claims, 7 Drawing Sheets

(51) Int. Cl.
  *A61M 5/32* (2006.01)
  *A61M 5/24* (2006.01)
(52) U.S. Cl.
  CPC . *A61M 2005/206* (2013.01); *A61M 2005/208* (2013.01); *A61M 2005/2407* (2013.01)

AUTO-INJECTOR WITH PIVOTING TRIGGER

FIELD OF THE DISCLOSURE

The present invention relates to a trigger mechanism for an auto-injector, specifically to a resettable trigger mechanism for a reusable and resettable auto-injector device.

BACKGROUND

Reusable auto injectors that can be loaded with a container subassembly, such as a syringe, are known in the prior art. For example, U.S. Pat. No. 5,599,309 discloses an auto injector for use with proprietary syringes comprising a drive member that receives the rear end of a plunger of a syringe and a trigger for releasing the drive member such that a medicament can be injected. Drawbacks with prior known device is that once the trigger is cocked there is no safety mechanism to prevent a user from accidentally pushing the trigger and firing the device before the auto-injector has been placed against an injection site.

SUMMARY OF THE INVENTION

It is therefore an object of the invention to provide a resettable trigger and mechanism for a reusable auto-injector that can only be fired once the injector is pushed against an injection site. Another object is to provide an injection device where the needle is kept non-visible to the user at all times and that the device is easily re-loadable and resettable. These objects and other objects are achieved by the reusable auto-injector and associated trigger mechanism disclosed below and as defined by the claims. A method reactivating and firing the auto-injector is also presented.

Thus, in accordance with an aspect of the present invention, there is provided trigger for an auto-injection device comprising an elongate body having longitudinal axis L and a pivot axis P, where axis P is approximately perpendicular to the L axis and divides the body of the trigger into a distal portion and a proximal portion. Preferably these two portion are approximately equal in length. The upper section of the proximal portion contains a finger surface configured to be pushed downwardly (inwardly) into the device outer housing by a user's finger causing the trigger to pivot about the P axis when the auto-injector is intended to be fired to initiate an injection. A bearing surface projects downwardly from the upper section of the proximal portion and is configured to engage a button blocker forming a safety feature that prevents the button from being pushed accidentally and before the injection device is pushed against an injection site. The button also has two axle studs each projecting outwardly from the elongate body along axis P. These axle studs are configured to fit within sockets on the inside of the rear end (proximal end) housing section such that the studs are rotatably engaged with the inner surface of the outer housing but are axially fixed to the housing. The engagement of the axle studs with the housing sockets allows the trigger to pivot about axis P when moving from a cocked position to a fired position and back again from a fired to a cocked position. When in the cocked position the trigger projects out of the outer housing of the rear housing member such that it extends upwards with an angled profile relative to the outer surface of the outer housing.

The trigger has at least one abutment arm on the distal portion of the trigger that is configured to engage a recess located on a plunger rod driver when the trigger is moved into the cocked position. The trigger also has a catch on the distal portion configured to engage the plunger rod driver when plunger rod driver is manually moved proximally during resetting of the drive mechanism of the reusable auto-injector. When the catch is engaged with and holds the plunger rod driver from being driven distally forward by a biasing force the trigger is in the cocked position. The distal portion of the trigger also has a slot adjacent to one of the axle studs configured to engage one arm of a biasing member such that the trigger is always biased towards a cocked position. The other arm of the biasing member abuts and engages the inside of the housing. Preferably, the biasing member is a torsion spring where the two arms are biased apart and away from each other. The torsion spring exerts a downward force on the slot pivoting the trigger about the axle studs and urging the proximal portion of trigger upward. The torsion spring is preferably mounted on one of the axle studs to provide a bearing surface for the spring and to prevent axial movement relative to the injector housing. As mentioned, axis P divides the elongate body in approximately equal halves such that the longitudinal length of the distal portion is approximately equal to the longitudinal length of the proximal portion.

The above-described trigger is part of a trigger mechanism that comprises a button or trigger configured as described above to pivot about the pivot axis P between a cocked position and a fired position. The mechanism also includes a button blocker configured to slide axially from a blocked position to a release position, where the blocked position prevents the button from moving from the cocked position to the fired position. When the button blocker has moved axially in the proximal direction to the release position this allows the button to move from the cocked position to the fired position. When the button blocker is in the blocked axial position the bearing surface on the lower surface of the proximal portion of the button engages an outer bearing surface on the proximal outer surface of the button blocker preventing the button from pivoting from the cocked position to the fired position.

The button blocker is biased in the distal direction by a second biasing member, preferably a compression spring, to keep the button blocker in the blocked position until a counter acting force overcomes this axial biasing force causing the button blocker to move in the proximal direction. This counter acting force results when the needle hider sleeve located in the front housing member, as described below, is pushed axially in the proximal direction as the injector is placed against an injection site.

The finger surface of the proximal portion of the button or trigger comprises essentially all of the upper section of the proximal portion. Stated differently, the finger surface is the only upper section of the button that is exposed outside of the injector housing. In the cocked position the finger surface extends above the housing in an angled position with the lowest height near the P axis and the maximum height at the most proximal end of the proximal portion. This angle is preferably less than or equal to 45 degrees and most preferably in the range of from approximately 30 to about 45 degrees.

The trigger mechanism also comprises a plunger rod driver that is engaged by the downwardly projection catch located on the distal portion of the button (trigger). The catch preferably is positioned between two abutment arms extending distally from the distal portion of the button. The catch projects downward, inwardly, or radially towards the centerline of the plunger rod driver and injector. A preferred shape of the catch is that resembling a knife-edge that has a bearing surface that engages a cutout in the outer surface of the plunger rod driver. This engagement acts as an axial stop preventing axial movement of the plunger rod driver. As the button pivots about the axle studs, with the finger surface being pushed downwardly or radially toward the centerline of the injector, the distal portion of the button pivots upward or radially outwardly from the centerline of the injector. As the distal portion moves upward the catch disengages from the cutout in the plunger rod driver and no longer acts as an axial stop preventing the plunger rod driver from moving forward axially in the distal direction. Because the plunger rod driver is under a biasing force from a third biasing member, preferably a compressed helical coil spring, urging it axially forward, the disengagement of the catch (i.e., removal of the axial stop) frees the plunger rod driver to slide forward as the biasing member pushes it distally.

The cutout on the outer surface of the plunger rod driver is located at the distal end of the plunger rod driver sleeve. The outer surface also contains one or two recesses that are configured to accept the abutment arms when the trigger is moved (pivoted) from the fired position to the cocked position. After the trigger mechanism has been fired and the plunger rod driver has moved distally forward the recesses move out of engagement with the abutment arms as the distal end of the plunger rod driver moves distally. Preferably, each recess is configured with a slope or an incline surface such that as the plunger rod driver moves distally the abutment arms are forced to move radially outward from the centerline causing the button to pivot about the P axis. Once the recess has moved distally past the abutment arm the outer surface of the plunger rod driver will engage the abutment arm and will act as a bearing surface to prevent the distal portion of the button from pivoting downwardly and raising the finger surface upward at an angle relative to the outer surface of the injector outer housing. In this fired position the finger surface of the proximal portion of the button is essentially parallel to the outer housing and the angle is essentially zero. In some cases it may be desirable to have the finger surface become flush with the outer surface of the injector housing. When the button is in the fired position the user is provided with both a visual and tactile signal that the injector is not cocked and that the injector was successfully fired. Likewise, when the button is in the cocked position and projects out of the injector housing at an angle, as described above, the user is presented with both a visual and tactile indication that the injector is in a cocked state and can be fired once the needle hider is pushed against an injection site.

A method of activating and firing a resettable auto-injector is also presented where the steps include first separating the front housing member of the auto-injector from the rear housing member. The front housing member holds the container of medicament, preferably as a pre-filled syringe with an attached needle and needle shield in place. The rear housing member contains the firing or drive mechanism that acts on the on the syringe and the syringe plunger to move the syringe distally to insert the injection needle into the injection site followed by pushing the syringe plunger and piston distally to inject the medicament. When the front housing member is separated from the rear housing member a new prefilled syringe can be inserted to replace a spent (empty) syringe.

A needle shield remover can be used as a resetting tool that is configured to also allow adjustment of the needle hider to set different depths of injection. When used as a resetting tool associated the needle shield remover is used to reset the firing or drive mechanism in the rear housing member. The needle shield remover is inserted into the rear housing and pushed proximally to engage and push the plunger rod driver proximally from its most distal position to the cocked position where the downwardly projecting catch on the button snaps into the cut-out on the outer surface of the distal end of the plunger rod driver to create an axial stop. Enough force must be used in pushing the needle shield remover proximally to overcome the third biasing member that exerts an axial biasing force in the distal direction against the plunger rod driver. As the plunger rod driver is moved proximally the abutment arms on the button move into the slope recesses on the outer surface of the plunger rod driver allowing the proximal section of the biased trigger or button to pivot upward exposing the finger surface at the angled position above the outer surface of the housing. Once the catch engages the plunger rod driver the button is in the cocked position.

The needle shield remover or resetting tool is then removed from the rear housing member and the front housing member, with the install pre-filled syringe, is re-connected to the rear housing member through a screw thread, snap fit, press fit, bayonet, luer-lok, detent, or similar connection that holds the two housing members in a secure manner. The needle shield remover is then used to remove the needle shield from the injection needle attached to the distal end of the syringe. The auto-injector is now in a cocked state and is ready for use. Although the trigger mechanism is in the cocked position the trigger cannot be fired because the button blocker is in the blocked position where its outer surface is engaged with the bearing surface on the lower portion of the proximal portion of the trigger. This engagement of the trigger bearing surface with a like bearing surface on the button blocker acts as a safety feature preventing the trigger from being pushed down and pivoting about the P axis and thus firing the auto-injector before the needle hider is pushed against an injection site.

To fire the auto-injector to inject the medicament contained in the pre-filled container or syringe, the user must push the needle hider against the injection site so that the needle hider moves proximally pushing the button blocker axially and overcoming a distal biasing force exerted by the second biasing member. This proximal movement of the button blocker compresses the second biasing member and moves the button blocker out of engagement with the bearing surface on a proximal portion of a button. The trigger is now unobstructed and is free to move downward in a pivotal movement about the P axis. The first biasing member exerts a torsional downward force on the distal portion of the trigger thus biasing the proximal portion and the finger surface upwards at an angled position relative to the outer housing of the auto-injector. The user can now apply a counter downward force to the finger surface to overcome the torsional upward force causing the proximal section of the trigger to pivot and rotate downwardly towards the centerline of the injector which in turn causes the distal portion of the trigger to move upwards, similar to how a child's seesaw operates. As the distal portion moves upwards the catch and the abutment arms disengage from the plunger rod driver. The third biasing member then causes the plunger rod driver to slide distally forward and pushes the syringe forward to complete the injection. By providing a needle hider at the distal end of the front housing member, the needle can be kept out of sight of a user, which eases the anxiety of those users who suffer from needle phobia.

In a particular embodiment of the medicament injection device according to the invention, the needle shield remover and the needle hider are arranged to mate with each other such that axial movement of the needle shield remover relative to the needle hider front is allowed while rotation of the needle shield remover relative to the needle hider front is prevented. This arrangement allows a user to use the needle shield remover to adjust the axial position of the front of the needle hider that is connected by a threaded connection to the needle hider body by holding the front housing while turning the needle shield remover. The needle hider body can be configured to be axially moveable within the front housing member between a proximal end position and a distal end position and wherein a syringe guide is arranged within said needle hider body for receiving a replaceable container of medicament, such as a prefilled syringe, where the syringe guide is axially moveable between a proximal end position and a distal end position relative to the front housing member and wherein a distal end surface of the syringe guide defines a maximum insertion depth for the needle shield remover. The distal end surface of the syringe guide defines the maximum insertion depth of the needle shield remover and acts as an abutment such that the front housing member can be used to relocate the drive mechanism in the rear housing member.

The penetration depth of the injection needle can be adjusted by adjusting the position of the needle hider front using the needle shield remover. A threaded connection of the needle hider front to the needle hider body is a preferred configuration to provide an adjustable penetration depth. The needle hider front can also have visible indicium that presents to the user the needle penetration depth. The indicia can be in the form of numerals visible in a window or opening in the front housing clearly indicating the currently set penetration depth.

The needle shield remover can have one or more flexible hooks arranged to grasp the needle shield of the injection needle such that when the needle shield remover is inserted into the distal end of the front housing through the needle hider front the flexible hook will deflect over the outer surface of the needle shield and as soon as the flexible hook passes the proximal end of the needle shield it will flex back to a less biased position and the hook, preferably provided with a fluke, or barbed element, will securely grasp the needle shield such that when the needle shield remover is pulled out of the front housing, the needle shield will be pulled off the injection needle.

These as well as other advantages of the various aspects of the trigger mechanism of the invention, and the manner of attaining them, will become apparent to those of ordinary skill in the art by reading the following detailed description, with appropriate reference to the accompanying drawings.

BRIEF DESCRIPTION OF THE DRAWINGS

The invention will now be described in more detail and with reference to the appended drawings in which.

DETAILED DESCRIPTION

As used herein, the term "container" encompasses all types of containers suitable for injectable liquid composition. Concerning the terms "distal" and "proximal" they refer to points that are closer to and further away from the injection site, respectively. So, for example, the needle hider of the reusable auto-injection device described herein is located at the distal end of the injector and the trigger is located at the proximal end.

Figure 1A:
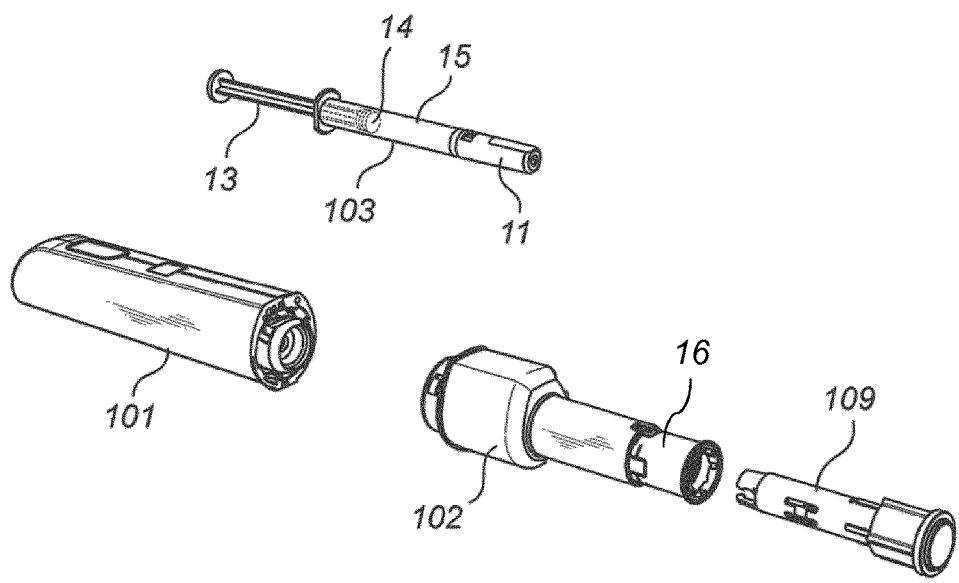
FIG. 1a is a schematic perspective view of an embodiment of the medicament delivery device according to the invention in a disassembled state.
Figure 1B:
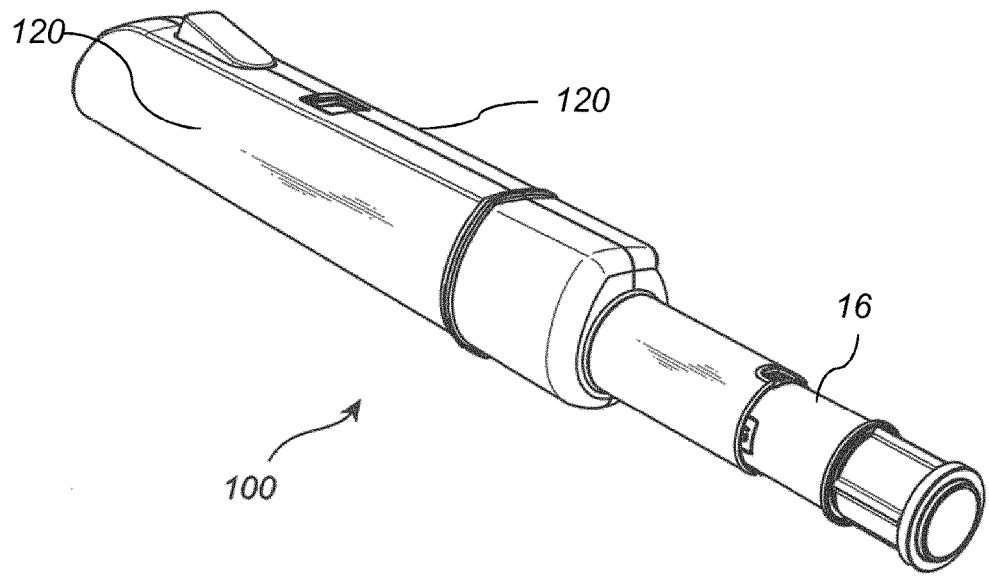
FIG. 1b is a schematic perspective view of an embodiment of the medicament injection device according to the invention in an assembled state.

In one embodiment a reusable auto-injection device 100 according to the invention, as shown in FIGS. 1a and 1b, comprises a rear housing member 101 made from e.g. thermoplastic, a front housing member 102 and a replaceable container subassembly 103, such as a syringe. The rear housing member 101 can be made up of two halves of outer housing 120 which are secured to each other by means of pins or projections provided at one of the halves and corresponding openings in the other half. Obviously, other solutions are imaginable, such as tongue and groove solutions; snap catch elements; or even permanent securing with welding or gluing.

The rear and front housings members 101, 102 are connectable to each other by e.g. a twisting coupling or any other connector that secures the two housing members to make a unitary device. Preferably, the front and rear housing members 101, 102 can be connected and disconnected by a 90 degree relative twist of the housing members 101, 102. The replaceable container subassembly 103 may comprise an injection needle (not shown), a medicament container 15, a piston 14, a plunger or piston rod 13 and a needle shield 11 arranged to completely cover and protect users from the injection needle. Obviously, it is also imaginable that the container subassembly 103 lacks a plunger rod 13 and that the rear housing member contains a piston rod that is reusable and resettable.

Figure 2:
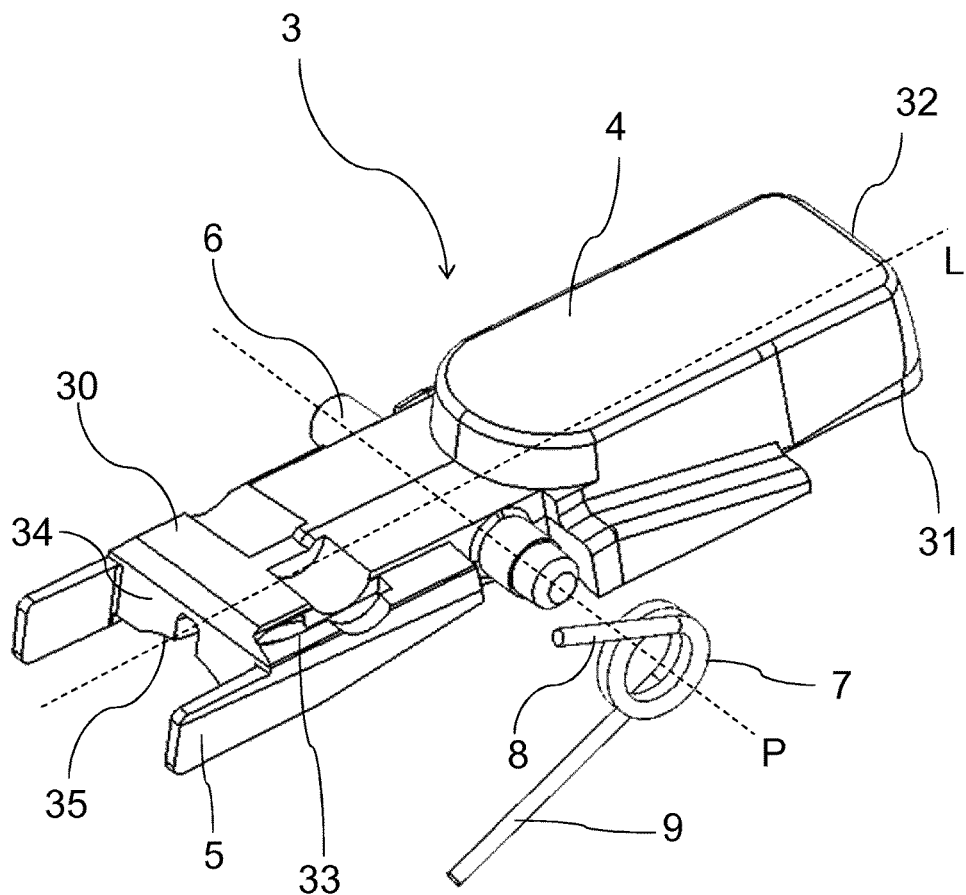
FIG. 2 is a perspective view of the trigger and the first biasing member according to the invention.
Figure 3:
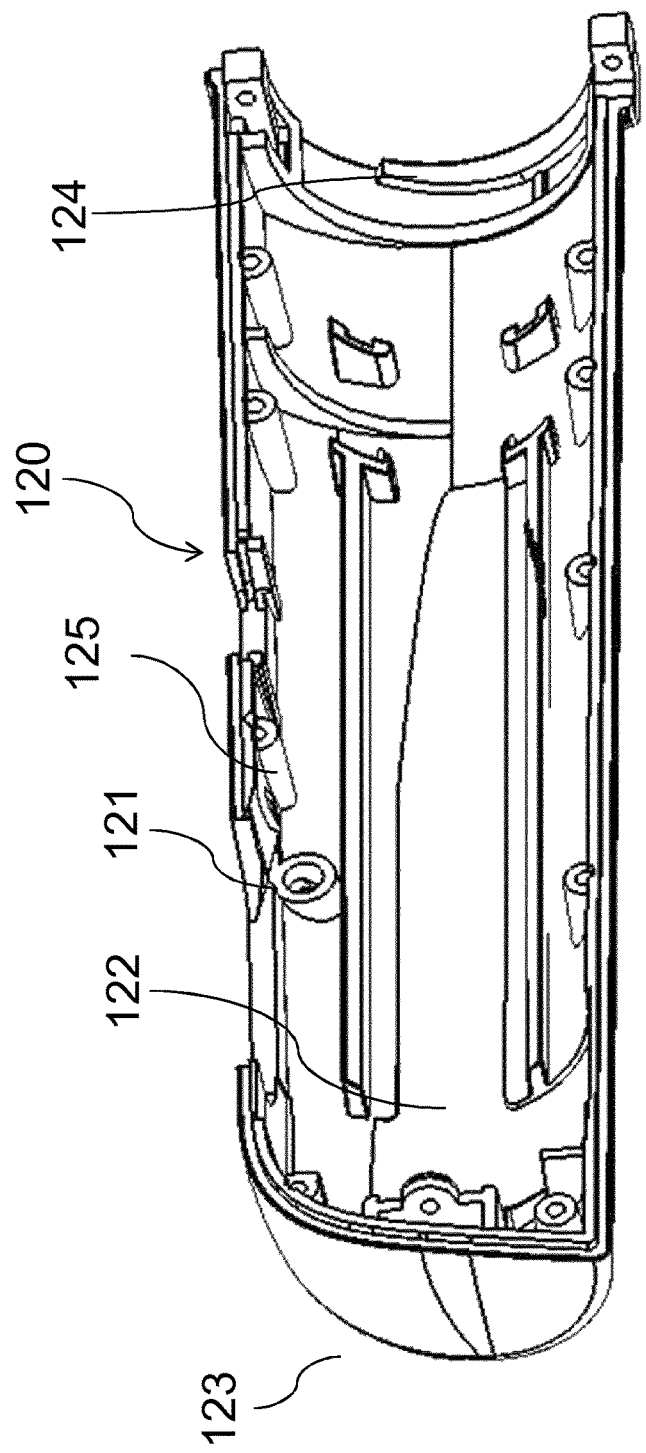
FIG. 3 is a perspective side view of one halve of the outer housing of the rear housing member according to the invention.

FIG. 2 illustrates one embodiment of the trigger or button 3 of the invention. Reference axes P and L are perpendicular to each other with the P axis defining a pivoting line that runs through axle studs 6 that protrude outwardly at right angles from the longitudinal axis L. The two axle studs are configured to fit into sockets located on the inside surface of each half of the outer housing 120 of the rear housing member 101. FIG. 3 illustrates one half of the outer housing 120 and a socket 121 on an inner surface 122. A similar socket is found on the other half of the outer housing. When connected together the two halves form the outer housing of the rear housing member 101. The sockets and axle studs are configured such that the axle studs freely rotate within the sockets but are axially fixed relative to the outer housing 120. The outer housing 120 has a proximal end 123 and a distal end 124 that receives the front housing member 102 when the injector is assembled for use.

The trigger 3 has a proximal portion 32 and a distal portion 30, each of which are approximately the same longitudinal length with the midway point defined approximately by the P axis. The distal end of the trigger 3 is shown with two abutment arms 5 with a catch 34 located between the arms and projecting downward toward the centerline of the injection device (see FIG. 5a). Catch 34 has a downwardly projecting bearing surface 35 that is configured to act an axial stop that engages a cutout in the distal end of a plunger rod driver 1. The distal portion 30 also has a slot 33 that is configured to accept arm 9 of biasing member 7, shown as a torsion spring. The other arm 8 of spring 7 abuts a top inner surface 125 of outer housing 120 (see FIG. 3). Slot 33 is configured such that arms 8 and 9 are biased away and apart from each other. Since inner housing surface 125 is fixed, arm 8 is fixed and prevented from moving. This causes arm 9 to exert a downward biasing force on the slot of distal portion 30. Because axle studs 6 are axially fixed in the sockets 121, this biasing force urges the distal portion 30 to pivot about the axle studs 6. If the distal portion 30 is allowed to pivot downward this will cause the proximal portion 32 to pivot upwardly away from the centerline C. As described in more detail below, if there is no structure to oppose the pivoting of the distal portion 30 then the trigger will assume the cocked position where the proximal portion projects outward from the outer surface of outer housing 120 at an angle A (see FIG. 5a).

Figure 4:
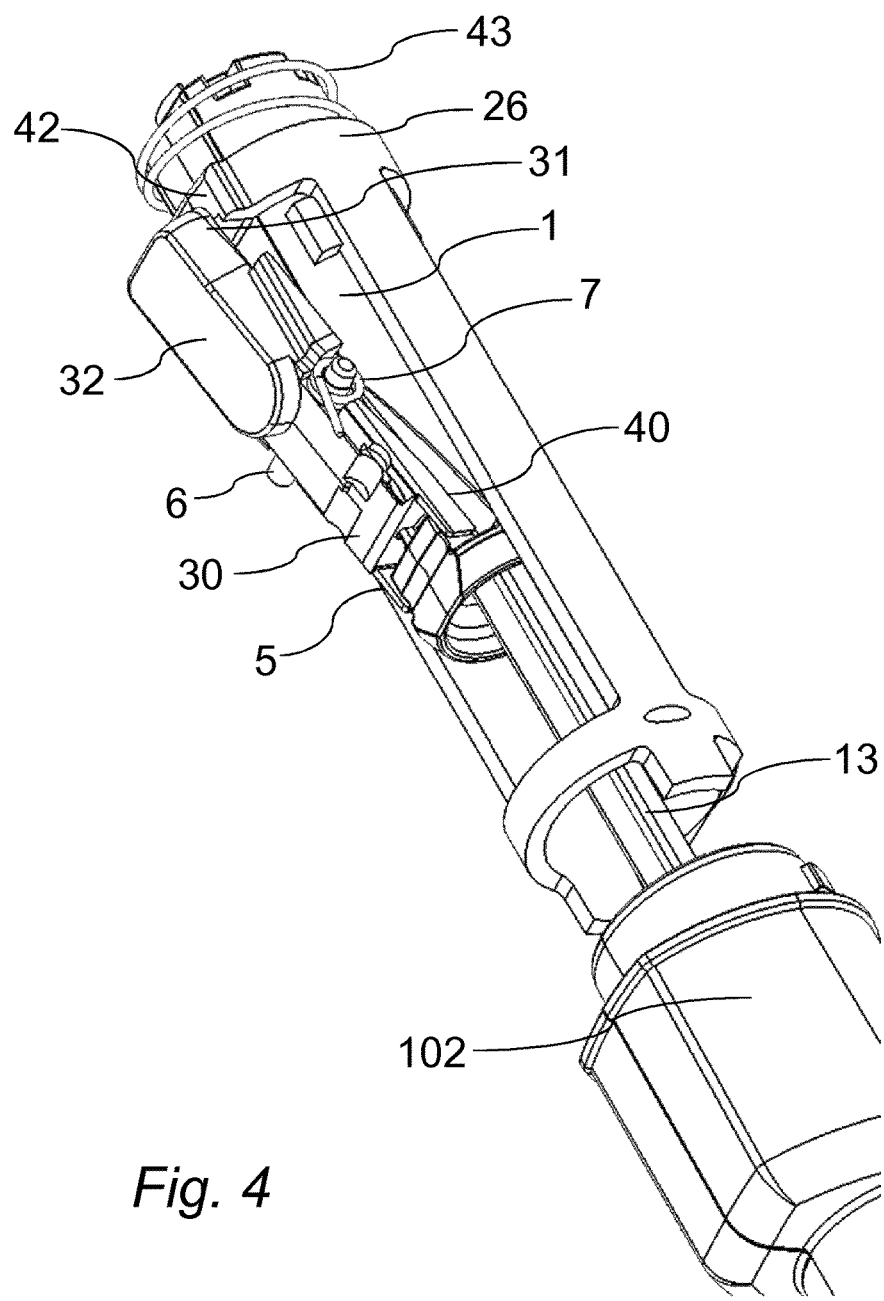
FIG. 4 is a perspective view of an embodiment of the rear housing member with the outer housing removed.

The upper surface of the proximal portion 32 defines a finger surface 4 that comprises substantially the entire upper portion of the proximal portion 32. At the bottom surface of proximal portion 32 is a bearing surface 31 that is configured to engage a like bearing surface 42 on button blocker 26 as described in more detail below. FIG. 4 shows the drive mechanism that is contained in the rear housing member 101 with both halves of the outer housing 120 removed and with the trigger mechanism in the cocked position. The bearing surface 31 of the proximal portion 32 of trigger 3 is abutting and engaged with a like bearing surface 42 located on the outer surface of the proximal end of button blocker 26. This engagement of trigger 3 and button blocker 26 is a safety feature that prevents the trigger mechanism from moving from the cocked position to the released position before the injector has been placed against an injection site. The two bearing surfaces 31 and 42 act as a pivotal stop preventing the proximal portion 32 of the trigger 3 from pivoting downward causing the distal portion 30 to move upward in a seesaw motion releasing catch 34 from plunger rod driver 1. The button blocker 26 is urged distally in the blocked position by second biasing member 43, which is shown as a compression spring. In the cocked position the abutment arms are positioned in recesses 40 of the plunger rod driver 1. These recesses allow the distal portion 30 of trigger 3 to pivot downward to achieve the cocked position shown in FIG. 4. Plunger rod driver 1 is shown engaged with piston rod 13 of syringe 15, which is located in the front housing member 102.

Figure 5A:
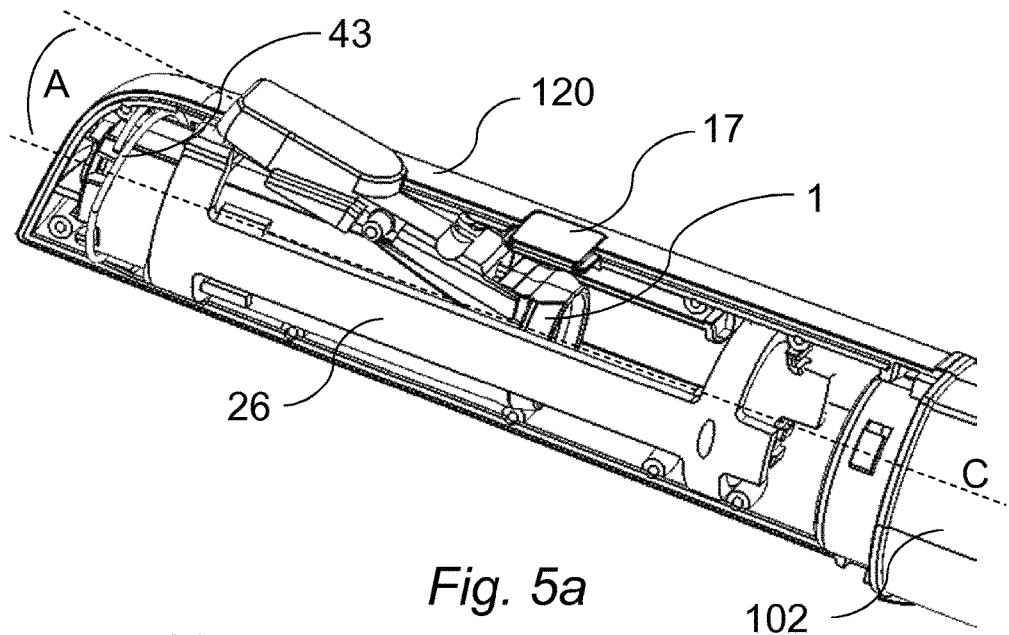
FIG. 5a is a perspective cross-section of an embodiment of the rear housing member with half of the outer housing removed, the trigger is in the cocked position, and the button blocker in the blocked position.
Figure 5B:
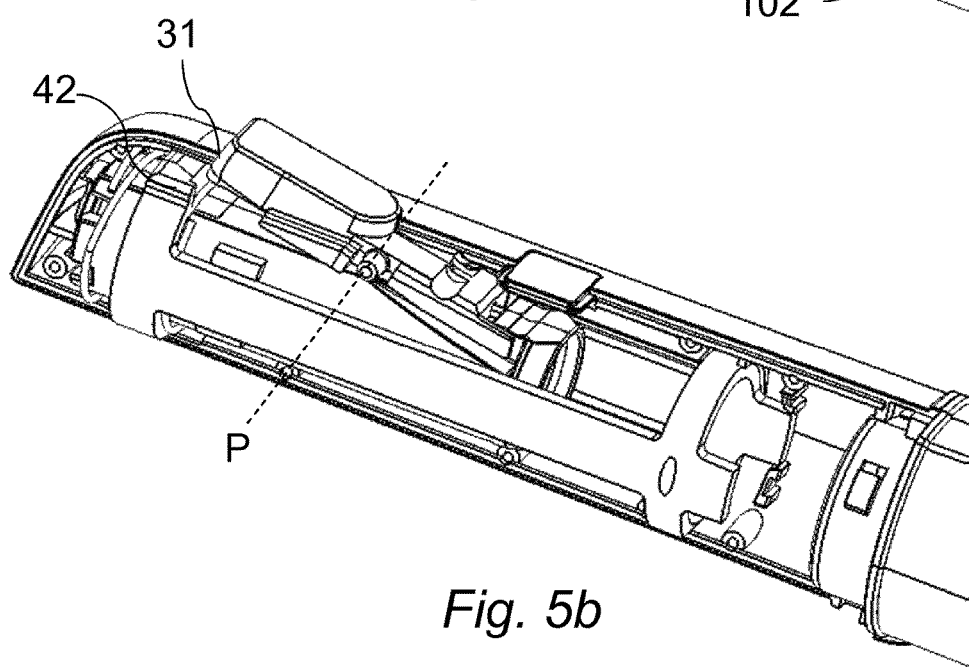
FIG. 5b is a perspective cross-section of an embodiment of the rear housing member with half of the outer housing removed, the trigger is in the cocked position, and the button blocker in the released position.
Figure 5C:
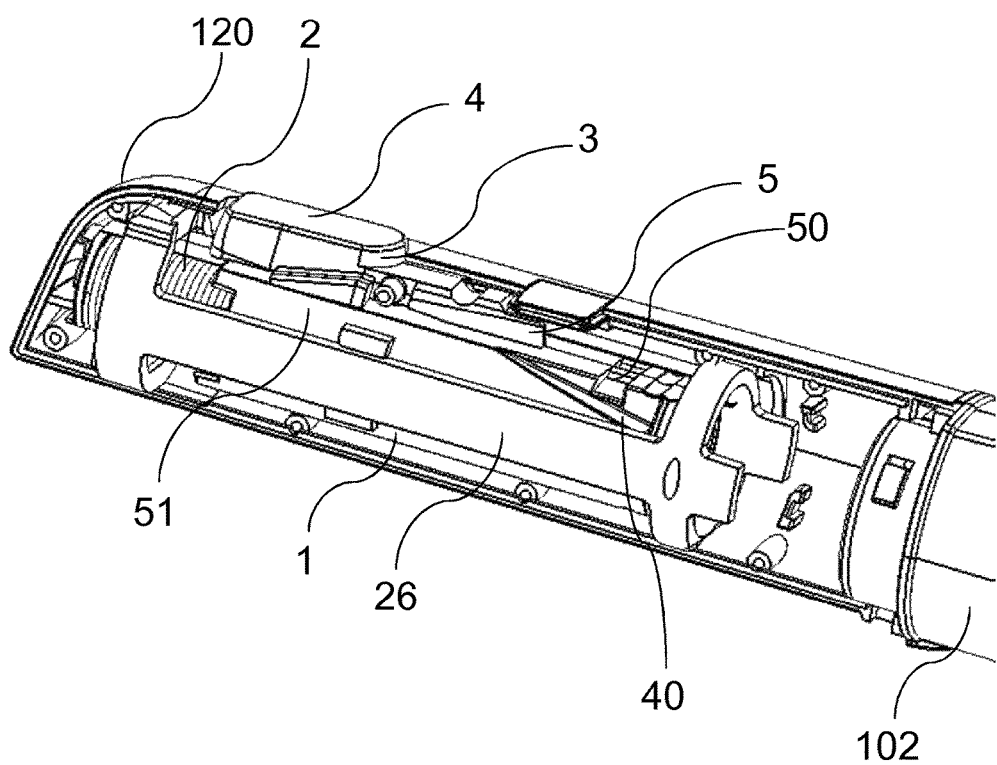
FIG. 5c is a perspective cross-section of an embodiment of the rear housing member with half of the outer housing removed, the trigger is in the released position and the button blocker in the released position.

FIGS. 5a-5c illustrate the trigger mechanism in the three possible positions. FIG. 5a is where the trigger 3 is cocked, but cannot be fired because button blocker 26 is in the blocked position where the biasing surfaces 42 and 31 are in contact with one another preventing downward rotation (pivoting) of the proximal portion 32 of trigger 3. In the cocked position trigger 3 is raised above the outer housing 120 by an angle A, which is preferably in the range from about 30 to about 45 degrees. Spring 43 exerts a distal biasing force on button blocker 26 to keep biasing surfaces 42 and 31 in contact and thus providing the safety feature that the trigger mechanism cannot be fired prematurely, i.e., before the needle hider 16 is pressed against an injection site. This raised button 3 provides both a visual and tactile signal to the user that the trigger mechanism is in the cocked position and is ready to perform an injection. Additionally, outer housing 120 can contain a window 17 that allows the user to see indicia (color, numbers or the like) on the plunger rod driver 1 that indicates it is in a cocked or loaded position. The status window 17 is preferably made of a transparent, or at least translucent, plastic material. After firing, i.e., performing the injection, the plunger rod driver will move (slide) to its most distal position and the window will then reveal indicia indicating that the injection is complete.

FIG. 5b illustrates the trigger mechanism when the needle hider (not shown) has been pushed against an injection site causing the button blocker to move (slide) proximally compressing spring 43. This proximal movement disengages bearing surfaces 31 and 42, thus removing the pivotal stop (i.e., the safety feature) that prevents the proximal portion of the trigger from pivoting downwardly about axle studs 6 and axis P. FIG. 5c illustrates the trigger mechanism in its third or fired position where the user has pushed on finger surface 4 causing button 3 to pivot about axis P reducing the angle A between axes L and C to approximately zero degrees. The button 3 is now essentially flush with outer housing surface 120. As the proximal portion of trigger 3 pivots downward the distal portion pivots upward and disengages catch 34 from cutout 50 in the distal portion of plunger rod driver 1 freeing it to move (slide) distally as a result of the biasing force of the third biasing member 2, shown as a helical coil spring. As spring 2 expands it pushes the plunger rod driver 1 distally until it reaches a predetermined stop. This movement of syringe 15 forward causes the injection needle to move distally out of the distal end of the needle hider to penetrate tissue at the injection site. The plunger rod driver continues to move forward driving plunger rod 13 distally, which in turn moves piston 14 within the syringe barrel to expel the medicament through the injection needle and into the penetrated tissue.

Figure 6:
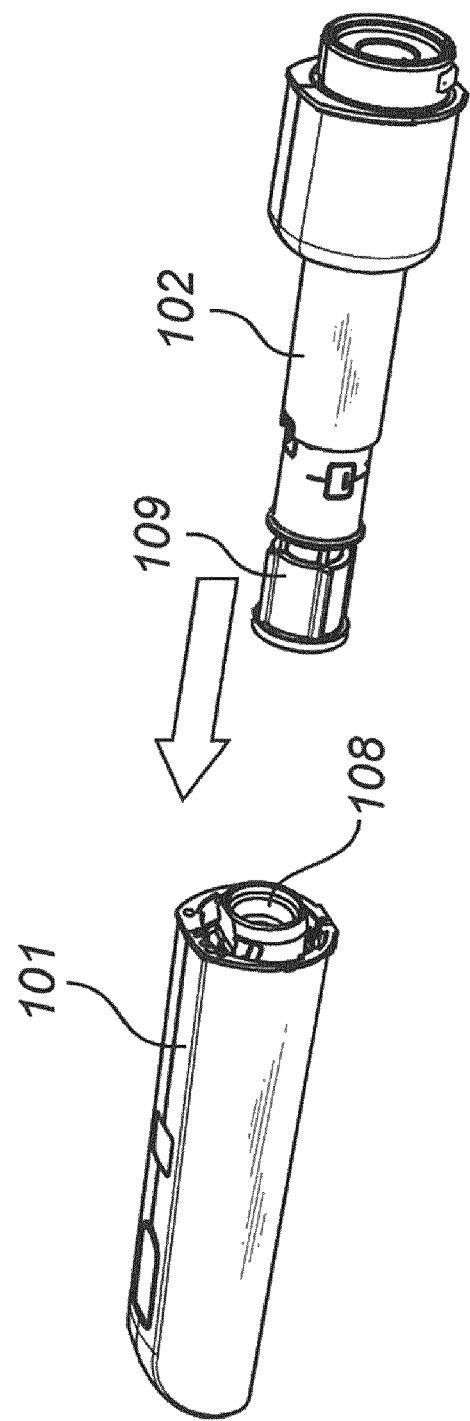
FIG. 6 is a perspective side view of a resetting orientation of the rear housing member with the front housing member containing a resetting tool according to the invention.

When the trigger mechanism has fired, as shown in FIG. 5c, abutment arms 5 move out of engagement with recesses 40 as the angled surfaces of recesses 40 push the distal end of the trigger upwards such that they are now are engaged with the outer surface 51 of the plunger rod driver 1. In this position the abutment arms will prevent the trigger 3 from returning to the angled elevated cocked position shown in FIG. 5a. In order to reset the drive mechanism of rear housing member 101 the injector must first be disassembled by disconnecting the rear housing member 101 from the front housing member 102. Once disconnected, a resetting tool, such as needle shield remover 109, is inserted into the distal end 124 of rear housing member 101 and is used to push plunger rod driver 1 proximally. One preferred method is illustrated in FIG. 6 where the needle shield remover 109 being inserted into the distal end of front housing member 102 is used to insert the distal end of needle shield remover 109 into the distal end 124 of rear housing member 101 to push plunger rod driver 1 in the proximal direction.

As plunger rod driver is pushed proximally, abutment arms 5 will move into the sloped recesses 40 as a result of the pivoting downward biasing force exerted by torsion spring 7 on the distal portion 30 of trigger 3. As the plunger rod driver continues to move proximally by the action of the needle shield remover 109, or the like resetting tool, the distal portion of the trigger 3 will continue to pivot downward until the abutment arms 5 fully engage recesses 40 and the catch 34 locks into cutout 50 acting as a distal stop to prevent the plunger rod driver 1 from moving distally forward. During resetting of the plunger rod driver 1 the axial force exerted by spring 2 is overcome and the spring compresses to a charged state. Because the needle hider 16 is no longer pushed against an injection site and the injector is disassembled there is no axial force in the proximal direction exerted on the distal end of button blocker 26. This allows spring 43 to bias and move the button blocker from the release position to the blocked position. Since the trigger 3 has pivoted about axis P as a result of the torsional force generated by spring 7, the proximal portion of trigger 3 is again elevated above the outer housing surface 120 to angle A. This allows bearing surfaces 42 and 31 to contact each other and resets the safety feature described above and as illustrated in FIGS. 4 and 5a.

Finally, it is realized, that a medicament injection device according to the invention has a number of advantages over the known prior art devices. Due to the fact that the device has a completely mechanical design, reliability can be ensured at all time without being dependent on batteries or similar. The trigger mechanism can be reset in a simple and reliable manner at the same time the drive mechanism is reloaded by using the front housing and the needle shield remover of the device itself. The needle hider front is biased with a fourth biasing member and always covers the needle such that the needle never will be visible to the patient. Penetration depth can also be set in a very simple and user-friendly manner. By using the needle shield remover as a grip, also users with reduced strength and/or co-ordination will be able to do this. The device is re-usable and the user can change the emptied syringe to add a new prefilled syringe in a simple manner. The device allows for a variable penetration depth and the setting of the dose can be set downwardly and upwardly until a required depth has been set.

It is to be understood that the embodiments described above and in the drawings are to be regarded only as non-limiting examples of the invention and that they may be modified in many ways within the scope of the claims. This application is therefore intended to cover any variations, uses or adaptations of the invention using its general principles. Further, this application is intended to cover such departures from the present disclosure as come within known or customary practice in the art to which this invention pertains.

I claim:

1. A trigger for an auto-injection device, comprising:
   an elongate body having a longitudinal axis L and a pivot axis P, wherein the pivot axis P divides the elongate body into a distal portion and a proximal portion;
   a finger surface on an upper section of the proximal portion, and a bearing surface projecting downwardly from the upper section of the proximal portion;
   two axle studs on the distal portion, each axle stud projecting outwardly along the pivot axis P and configured to rotatably engage a housing to allow the trigger to pivot about the pivot axis P from a fired position to a cocked position, wherein the bearing surface is configured to engage a button blocker in a blocked position, wherein the button blocker is axially slidable relative to the housing from the blocked position to a release position such that the button blocker disengages the bearing surface;
   an abutment arm on the distal portion configured to engage a plunger rod driver when the trigger is in the cocked position;
   a catch on the distal portion configured to prevent axial movement of a plunger rod driver when the trigger is in the cocked position; and
   a slot adjacent to one of the axle studs configured to engage one arm of a biassing member such that the trigger is biassed toward the cocked position.

2. The trigger of claim 1, wherein one of the axle studs holds the biassing member, wherein the one arm of the biasing member is a first arm and the biasing member comprises a second arm.

3. The trigger of claim 2, wherein the biassing member is a spring, the first arm engages the slot, and the second arm engages an interior portion of a housing structure of the auto-injection device.

4. The trigger of claim 2, wherein the biassing member is a torsion spring, and the first and second arms are biassed away from each other.

5. The trigger of claim 1, wherein the pivot axis P divides the elongate body in approximately equal halves such that a longitudinal length of the distal portion is approximately equal to a longitudinal length of the proximal portion.

6. The trigger of claim 1, further comprising two abutment arms projecting distally and parallel to the longitudinal axis L, wherein the catch is located between the two abutment arms and has a bearing surface projecting downwardly from an upper surface of the distal portion.

7. A trigger mechanism for a resettable auto-injection device, comprising: a button configured to pivot about a pivot axis P between a cocked position and a fired position, the button comprising an elongate body having a longitudinal axis L, wherein the pivot axis P divides the elongate body into a distal portion and a proximal portion; wherein the button further comprises a finger surface on an upper section of the proximal portion and a bearing surface projecting downwardly from the upper section of the proximal portion; a first biasing member configured to engage the button and exert a torsional force, thereby biassing the button toward the cocked position; a button blocker configured to slide axially from a blocked position to a release position, wherein the button blocker in the blocked position engages the bearing surface and prevents the button from moving from the cocked position to the fired position, and the button blocker in the release position is disengaged from the bearing surface and allows the button to move from the cocked position to the fired position; a second biasing member configured to engage the button blocker and bias the button blocker toward the blocked position; and an axially biased plunger rod driver releasably engaged with a catch on a distal portion of the button when the button is in the cocked position.

8. The trigger mechanism of claim 7, wherein the button comprises: two axle studs on the distal portion, each projecting outwardly along the pivot axis P and configured to rotatably engage a housing to allow the trigger to pivot about the pivot axis P from the fired position to the cocked position; two abutment arms on the distal portion configured to engage the plunger rod driver when the trigger is in the cocked position; the catch positioned between the abutment arms and having a bearing surface projecting downwardly from an upper surface of the distal portion configured to prevent axial movement of the plunger driver when the trigger is in the cocked position; and a slot adjacent to one of the axle studs configured to engage one arm of the first biassing member such that the trigger is biased toward the cocked position.

9. The trigger mechanism of claim 8, wherein the bearing surface projecting downwardly from the upper section of the proximal portion disengages from the button blocker when the trigger is moved to the cocked position and the button blocker is moved to the release position.

10. The trigger mechanism of claim 8, wherein the pivot axis P divides the elongate body in approximately equal halves such that a longitudinal length of the distal portion is approximately equal to a longitudinal length of the proximal portion.

11. The trigger mechanism of claim 8, wherein one of the axle studs holds the first biassing member, wherein the one arm of the first biasing member is a first arm, the first biassing member further comprising a second arm.

12. The trigger mechanism of claim 11, wherein the first biassing member is a spring, the first arm engages the slot, and the second arm engages an interior portion of a housing structure of the auto-injection device.

13. The trigger mechanism of claim 11, wherein the first biassing member is a torsion spring, and the first and second arms are biassed away from each other.

14. A trigger for an auto-injection device, comprising:
   an elongate body having a longitudinal axis L and a pivot axis P, wherein the pivot axis P divides the elongate body into a distal portion and a proximal portion;
   a finger surface on an upper section of the proximal portion, and a bearing surface projecting downwardly from the upper section of the proximal portion;
   two axle studs on the distal portion, each axle stud projecting outwardly along the pivot axis P and configured to rotatably engage a housing to allow the trigger to pivot about the pivot axis P from a fired position to a cocked position;
   two abutment arms on the distal portion, the two abutment arms projecting distally and parallel to the longitudinal axis L;
   a catch on the distal portion configured to prevent axial movement of a plunger rod driver when the trigger is in the cocked position, wherein the catch is located between the two abutment arms and has a bearing surface projecting downwardly from an upper surface of the distal portion; and
   a slot adjacent to one of the axle studs configured to engage one arm of a biassing member such that the trigger is biased toward the cocked position.

15. The trigger of claim 14, wherein the pivot axis P divides the elongate body in approximately equal halves such that a longitudinal length of the distal portion is approximately equal to a longitudinal length of the proximal portion.

16. The trigger of claim 14, wherein one of the axle studs holds the biassing member, wherein the one arm of the biasing member is a first arm and the biasing member comprises a second arm.

17. The trigger of claim 16, wherein the first and second arms of the biassing member extend distally from the axle stud.

18. The trigger of claim 16, wherein the biassing member is a spring, the first arm engages the slot, and the second arm engages an interior portion of a housing structure of the auto-injection device.

19. The trigger of claim 16, wherein the biassing member is a torsion spring, and the first and second arms are biassed away from each other.

* * * * *